United States Patent [19]

Kaplan et al.

[11] Patent Number: 4,492,695
[45] Date of Patent: Jan. 8, 1985

[54] THERAPEUTICALLY USEFUL IMIDAZO[1,2-A]PYRIDINE DERIVATIVES

[75] Inventors: Jean-Pierre Kaplan, Bourg la Reine; Pascal George, Vitry; Jean-Michel Bernardon, Chilly Mazarin, all of France

[73] Assignee: Synthelabo, Paris, France

[21] Appl. No.: 484,611

[22] Filed: Apr. 13, 1983

[30] Foreign Application Priority Data

Apr. 21, 1982 [FR] France ............... 82 06841

[51] Int. Cl.³ .................. A61K 31/435; C07D 471/04
[52] U.S. Cl. .................. 424/246; 424/248.54; 424/248.57; 424/256; 544/58.4; 544/127; 544/362; 546/121
[58] Field of Search .............. 546/121; 544/58.6, 127, 544/362; 424/248.54, 246, 248.57, 256

[56] References Cited

U.S. PATENT DOCUMENTS 4,382,938 5/1983 Kaplan et al. ............... 546/121

Primary Examiner—Henry R. Jiles
Assistant Examiner—Bernard I. Dentz
Attorney, Agent, or Firm—Wegner & Bretschneider

[57] ABSTRACT

An imidazo[1,2-a]pyridine derivative of the formula:

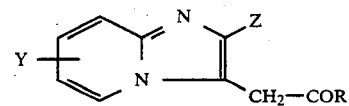

wherein Y represents a hydrogen or halogen atom or a $C_{1-4}$ alkyl radical, Z represents a furan-2-yl, thien-2-yl or pyridin-2-yl radical optionally carrying a halogen atom or a methyl or ethyl radical in the 5-position, and R represents the hydroxy radical, a $C_{1-4}$ alkoxy radical or a group —$NR_1R_2$ in which $R_1$ and $R_2$ independently of one another each represent a hydrogen atom; a straight- or branched-chain $C_{1-5}$ alkyl radical optionally carrying one or more halogen atoms or a hydroxy radical, a group —$N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical, or alternatively —$NR_1R_2$ together represent a heterocyclic ring containing from 3 to 6 carbon atoms, or a heterocyclic ring of the formula

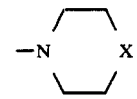

in which X is O, S, CHOR' or N-R'', R' being a hydrogen atom or the benzyl radical and R'' being a hydrogen atom, a $C_{1-4}$ alkyl radical or the phenyl radical optionally carrying a methoxy radical or a halogen atom, are new compounds. They are therapeutically useful as they possess anxiolytic, antianoxic, sleep-inducing, hypnotic and anticonvulsant properties.

12 Claims, No Drawings

THERAPEUTICALLY USEFUL IMIDAZO[1,2-A]PYRIDINE DERIVATIVES

DESCRIPTION

The present invention relates to new therapeutically useful imidazo[1,2-a]pyridine derivatives, to a process for their preparation and to pharmaceutical compositions containing them.

Imidazo[1,2-a]pyridines have already been described in the literature, for example in British Pat. Nos. 991,589 and 1,076,089 and in various other publications.

The imidazo[1,2-a]pyridine derivatives of the present invention are those compounds of the general formula:

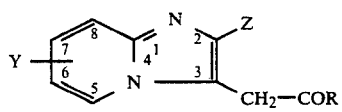

wherein Y represents a hydrogen or halogen (preferably chlorine) atom or a $C_{1-4}$ alkyl (preferably methyl) radical, Z represents a furan-2-yl, thien-2-yl or pyridin-2-yl radical optionally carrying a halogen (preferably chlorine or bromine) atom or a methyl or ethyl radical in the 5-position, and R represents the hydroxy radical, a $C_{1-4}$ alkoxy (preferably ethoxy) radical or a group —$NR_1R_2$ in which $R_1$ and $R_2$ independently of one another each represent a hydrogen atom; a straight- or branched-chain $C_{1-5}$ alkyl radical optionally carrying one or more halogen atoms or a hydroxy radical, a group —$N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical, or alternatively -$NR_1R_2$ together represent a heterocyclic ring containing from 3 to 6 carbon atoms, or a heterocyclic ring of the formula $$-N\diagup\diagdown X$$

in which X is O, S, CHOR' or N-R", R' being a hydrogen atom or the benzyl radical and R" being a hydrogen atom, a $C_{1-4}$ alkyl radical or the phenyl radical optionally carrying a methoxy radical or a halogen atom, and pharmaceutically-acceptable acid addition salts thereof.

Of particular interest are those compounds of general formula (I) wherein the symbol R represents the hydroxy radical, a $C_{1-4}$ alkoxy radical (preferably ethoxy), or a group —$NR_1R_2$ in which $R_1$ and $R_2$ both represent hydrogen atoms, or $R_1$ represents a hydrogen atom and $R_2$ represents a $C_{1-5}$ alkyl radical, or $R_1$ and $R_2$ both represent $C_{1-5}$ alkyl radicals. Examples of such groups —$NR_1R_2$ are amino, monomethylamino, dimethylamino, diethylamino and dipropylamino.

The preferred compounds of the invention are those wherein R represents a group —$NR_1R_2$ in which $R_1$ and $R_2$ are both hydrogen atoms or $C_{1-5}$ alkyl radicals, and amongst these the more particularly preferred compounds are those in which Y is in the 6-position and represents either a halogen (preferably chlorine) atom or the methyl radical.

Preferably the symbol Z in general formula (I) represents a thien-2-yl radical carrying a halogen atom or a methyl or ethyl radical in the 5-position.

Of outstanding importance are 6-methyl-N,N-dimethyl-2-(5-methylthien-2-yl)-imidazo[1,2-a]pyridine-3-acetamide, 6-methyl-N,N-dimethyl-2-(5-ethylthien-2-yl)-imidazo[1,2-a]pyridine-3-acetamide, 6-chloro-N,N-dimethyl-2-(5-chlorothien-2-yl)-imidazo[1,2-a]pyridine-3-acetamide and 6-chloro-N,N-dipropyl-2-(5-chlorothien-2-yl)-imidazo[1,2,a]pyridine-3-acetamide, and their pharmaceutically-acceptable acid addition salts.

According to a feature of the invention, the imidazo[1,2-a]pyridine derivatives of general formula (I) are prepared according to the following reaction scheme:

wherein 'alk' represents a $C_{1-4}$ alkyl radical and the other symbols are as hereinbefore defined.

The reaction for converting the nitrile of general formula (II) to an acid of general formula (I), viz R=OH, is carried out by a conventional known method, for example using potassium hydroxide in ethanol at the reflux temperature, or using acetic acid and concentrated hydrochloric acid at the reflux temperature.

The conversion of the acid (I, R=OH) to an ester (R=Oalk) is carried out by any suitable esterification method, for example by reacting the acid with sulphonyl chloride and the corresponding alcohol.

The conversion of an acid (I, R=OH) or ester (I, R=Oalk) to an amide is carried out by any suitable known method, for example either by reacting the acid with carbonyldiimidazole and then treating the product with a compound $HNR_1R_2$, or by reacting the ester with a compound $HNR_1R_2$, $R_1$ and $R_2$ being as hereinbefore defined.

The starting nitriles of general formula (II) are obtained either by a method described in the literature, in particular in British Pat. No. 1,076,089, or according to the following reaction scheme:

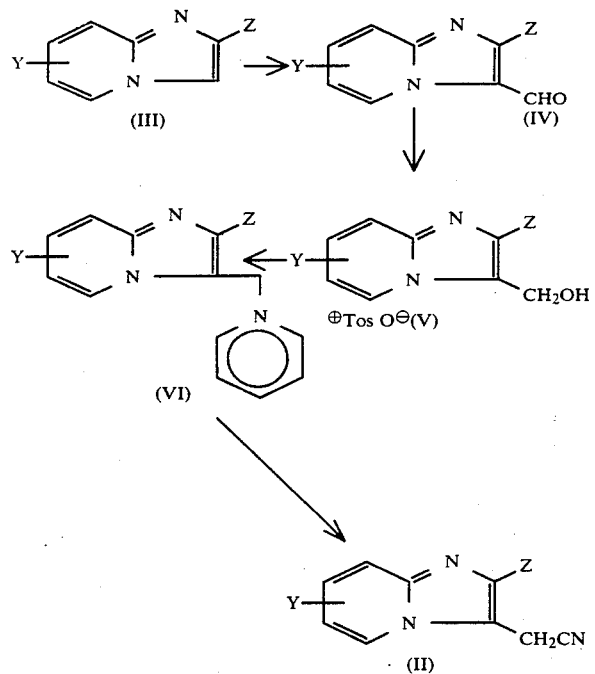

wherein Y and Z are as hereinbefore defined.

A starting material of general formula (III) can be obtained by condensing a substituted 2-aminopyridine:

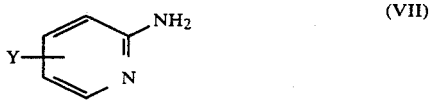

(wherein Y is as hereinbefore defined) with an α-bromoketone of the formula $ZCOCH_2Br$, wherein Z is as hereinbefore defined.

The aldehyde of formula (IV) is then prepared by any suitable method, for example by formylating the compound of formula (III) with dimethylformamide chloride. The aldehyde of formula (IV) is reduced to the alcohol of formula (V), for example using sodium borohydride. The pyridinium tosylate of formula (VI) is prepared by tosylating the alcohol of formula (V) in pyridine, and, finally, the pyridinium tosylate of formula (VI) is converted to the nitrile of formula (II) in an aqueous medium.

Pharmaceutically-acceptable acid addition salts of the imidazo[1,2-a]pyridine derivatives of general formula (I), e.g. methanesulphonates, mandelates, fumarates, maleates, malonates, citrates, hydrochlorides, hydrobromides and hydroiodides, may be obtained by methods known per se, for example by treatment of the imidazo[1,2-a]pyridine base with the appropriate acid in a solvent medium, e.g. an alkanol or ether, or mixtures thereof.

By the term 'methods known per se' as used in this specification is meant methods heretofore used or described in the literature.

The following Examples illustrate the invention.

The analyses and the IR and NMR spectra confirm the structures of the compounds.

EXAMPLE 1

6-Chloro-2-(pyridin-2-yl)-imidazo[1,2-a]pyridine-3-acetonitrile 1. 200 g (0.711 mol) of 2-bromoacetylpyridine hydrobromide, 91.5 g (0.711 mol) of 2-amino-5-chloropyridine, 179.4 g (2.135 mols) of $NaHCO_3$ and 500 ml of ethanol are introduced into an Erlenmeyer flask. The mixture is heated gradually to 40° C. and kept at this temperature for 4 hours. The solid is filtered off and extracted with a mixture of water and chloroform, and the organic phase is separated off, dried over magnesium sulphate and evaporated. The compound obtained is recrystallised from isopropyl alcohol.

Melting point = 190°–191° C.

2. 165 ml of dimethylformamide (DMF) are introduced into an Erlenmeyer flask; 50.77 g (0.4 mol) of oxalyl chloride are added dropwise, whilst cooling at −30° C. The mixture is stirred for 30 minutes at 0° C. and then allowed to return to ambient temperature. 22.9 g (0.1 mol) of 6-chloro-2-(pyridin-2-yl)-imidazo[1,2-a]pyridine (prepared as described in step 1) are added in small amounts and the mixture is stirred for 6 hours at ambient temperature and left to stand overnight. The reaction medium is poured into 500 ml of water and rendered alkaline with ammonia gas. The solid aldehyde product is filtered off and washed with water and then with acetone. It is triturated in boiling methanol.

Melting point = 227°–228° C.

3. 20 g (0.077 mol) of the aldehyde (prepared as described in step 2) in 300 ml of methanol are introduced into a round-bottomed flask. 1.45 g (0.0385 mol) of $NaBH_4$ in 10 ml of water are added dropwise and the mixture is stirred for 8 hours at ambient temperature. The mixture is evaporated to dryness and the solid residue is triturated in water, filtered off and washed with water. The 6-chloro-3-hydroxymethyl-2-(pyridin-2-yl)-imidazo[1,2-a]pyridine is extracted with chloroform and the organic phase is dried over $MgSO_4$ and evaporated. The residue is triturated in boiling isopropyl alcohol.

Melting point = 200°–201° C.

4. 5.2 g (0.02 mol) of the alcohol (prepared as described in step 3) and 50 ml of pridine are introduced into a round-bottomed flask. 4.2 g (0.022 mol) of p-toluenesulphonyl chloride are added and the mixture is stirred for 8 hours at ambient temperature. It is then evaporated to dryness and the residue is triturated in water. The solid is filtered off, washed with the minimum amount of acetone and dried in a desiccator Melting point = 220°–225° C.

5. 24.9 g (0.049 mol) of the pyridinium tosylate obtained as described in step 4, 7.2 g (0.147 mol) of NaCN and 300 ml of water are introduced into an Erlenmeyer flask. The mixture is heated at the reflux temperature for 2 to 5 hours, the suspension is cooled and the solid is filtered off and washed with water. It is then dissolved in chloroform, the organic phase is dried over $MgSO_4$ and evaporated, and the nitrile is recrystallized from ethyl acetate.

Melting point of the title product = 224°–225° C.

EXAMPLE 2

2-(5-Chlorothien-2-yl)-6-methylimidazo[1,2-a]pyridine-3-acetonitrile 1. 60 g (0.25 mol) of 2-bromoacetyl-5-chlorothiophene, 7.1 g (0.25 mol) of 5-methyl-2-aminopyridine, 42 g (0.5 mol) of $NaHCO_3$ and 300 ml of ethanol are introduced into an Erlenmeyer flask. The mixture is heated at 60° C. for 5 hours. It is then evaporated to dryness, the evaporation residue is taken up in a mixture of water and diethyl ether, and the solid is filtered off and dried in a desiccator in the presence of $P_2O_5$. The compound obtained is recrystallised from isopropyl alcohol.

Melting point = 188°-189° C.

2. 55 g (0.221 mol) of the compound obtained in step 1 and 400 ml of acetic acid are introduced into a round-bottomed flask. 37.4 g (0.331 mol) of dimethylamine, as a 40% solution in water, are added dropwise, the mixture is cooled to 0° C. and 24.8 g (0.247 mol) of formaldehyde, as a 30% solution in water, are added dropwise. The mixture is stirred for 4 hours and left to stand overnight. It is then evaporated to dryness, the residue is taken up in water, the mixture is rendered alkaline and extracted with chloroform, and the organic phase is separated off, dried over $MgSO_4$ and evaporated. The solid is taken up in 200 ml of methanol, and 41.9 g (0.296 mol) of methyl iodide are added. The mixture is stirred for 4 hours and left to stand overnight, and the ammonium iodide is filtered off and dried.

Melting point = 200°-205° C.

3. 86.5 g (0.193 mol) of the quaternary salt obtained in step 2, 28.4 g (0.579 mol) of NaCN and 1 liter of water are introduced into a reactor. The mixture is heated at the reflux temperature for 10 hours, the solid is filtered off, washed with water and dissolved in chloroform, the organic phase is dried over $MgSO_4$ and the solvent is evaporated off. The nitrile obtained is recrystallised from ethyl acetate.

Melting point of the title product = 167°-169° C.

EXAMPLE 3

6-Chloro-N,N-dimethyl-2-(5-bromofuran-2-yl)-imidazo[1,2-a]pyridine-3-acetamide

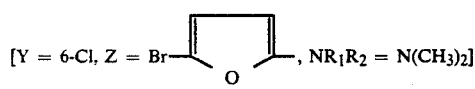

[Y = 6-Cl, Z = Br—furan, $NR_1R_2 = N(CH_3)_2$]

1. 40.5 g (0.12 mol) of 6-chloro-2-(5-bromofuran-2-yl)-imidazo[1,2-a]pyridine-3-acetonitrile, 33.6 g (0.6 mol) of potassium hydroxide and 1 liter of ethanol are introduced into a 2 liter three-necked round-bottomed flask. The reaction mixture is heated at the reflux temperature for 10 hours and evaporated, the residue is taken up in water and the mixture is then extracted with chloroform. The aqueous phase is acidified to pH 4.5 and the solid is filtered off, washed with water and then with the minimum amount of acetone and dried over $P_2O_5$.

Melting point = 255°-256° C.

2. 10 g (0.0281 mol) of the acid obtained in step 1 and 200 ml of tetrahydrofuran are introduced into an Erlenmeyer flask. 4.6 g (0.0281 mol) of carbonyldiimidazole are added in small amounts and the reaction mixture is stirred at ambient temperature for 5 hours. Excess dimethylamine is introduced and the reaction mixture is stirred for 4 hours. After evaporation to dryness, the residue is taken up in water, the mixture is rendered alkaline to pH 11 and the solid is filtered off. It is dissolved in chloroform and the solution is washed with water, dried over magnesium sulphate and evaporated.

Melting point of the title product = 252°-253° C.

EXAMPLE 4

6-Methyl-2-(5-methylthien-2-yl)-imidazo[1,2-a]pyridine-3-acetamide 1. 5.4 g (0.02 mol) of 6-methyl-2-(5-methylthien-2-yl)-imidazo[1,2-a]pyridine-3-acetonitrile, 11.2 g (0.2 mol) of potassium hydroxide and 300 ml of ethanol are introduced into an Erlenmeyer flask. The mixture is heated at the reflux temperature for 10 hours. It is then evaporated to dryness, the residue is dissolved in water and the solution is extracted with chloroform. The aqueous phase is decanted and acidified to pH 4, and the solid is filtered off, washed with water and dried in the presence of $P_2O_5$. The product is recrystallised from methanol.

Melting point = 230°-231° C.

2. 5 g (0.0174 mol) of 6-methyl-2-(5-methylthien-2-yl)-imidazo[1,2-a]pyridine-3-acetic acid (prepared as described in step 1) and 100 ml of tetrahydrofuran are introduced into an Erlenmeyer flask. 2.8 g (0.0174 mol) of carbonyldiimidazole are added in small amounts and the mixture is stirred at ambient temperature for 4 hours. 20 ml of tetrahydrofuran saturated with ammonia gas are introduced dropwise and the mixture is stirred for 4 hours. After evaporation to dryness, the residue is taken up in water and the mixture is rendered alkaline to pH 11; the solid is filtered off, washed with water and dried over $P_2O_5$. It is then recrystallised from isopropyl alcohol.

Melting point of the title product = 236°-237° C.

The compounds in the following Table were prepared, by way of Examples, according to the same reaction scheme.

TABLE

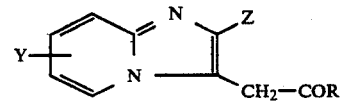

(I)

| Compound | Y | Z | R | Melting Point (°C.) |
|---|---|---|---|---|
| 1 | 6-Cl | Br—furan | $NH_2$ | 268–269 |
| 2 | 6-Cl | Br—furan | $N(CH_3)_2$ | 252–253 |
| 3 | 6-$CH_3$ | Br—furan | $NH_2$ | 266–267 |
| 4 | 6-$CH_3$ | Br—furan | $N(CH_3)_2$ | 250–251 |

TABLE-continued $$\text{(I)}$$

Structure: Y-pyridine ring with N=C(Z)-CH$_2$-COR substituent

| Compound | Y | Z | R | Melting Point (°C.) |
|---|---|---|---|---|
| 5 | 6-CH$_3$ | 5-methyl-2-furyl | NH$_2$ | 274–276 |
| 6 | 6-CH$_3$ | 5-methyl-2-furyl | N(CH$_3$)$_2$ | 220–221 |
| 7 | 6-CH$_3$ | 5-methyl-2-thienyl | NH$_2$ | 236–237 |
| 8 | 6-CH$_3$ | 5-methyl-2-thienyl | N(CH$_3$)$_2$ | 185–186 |
| 9 | 6-CH$_3$ | 5-ethyl-2-thienyl | N(CH$_3$)$_2$ | 156–157 |
| 10 | 6-Cl | 5-chloro-2-thienyl | NH$_2$ | 257–258 |
| 11 | 6-Cl | 5-chloro-2-thienyl | N(CH$_3$)$_2$ | 196–197 |
| 12 | 6-Cl | 5-chloro-2-thienyl | N(C$_3$H$_7$)$_2$ | 143–144 |
| 13 | 6-CH$_3$ | 5-chloro-2-thienyl | NH$_2$ | 245–246 |
| 14 | 6-CH$_3$ | 5-chloro-2-thienyl | N(CH$_3$)$_2$ | 197–198 |
| 15 | 6-Cl | 2-pyridyl | NH$_2$ | 241–242 |
| 16 | 6-Cl | 2-pyridyl | N(CH$_3$)$_2$ | 226–227 |
| 17 | 6-Cl | 2-pyridyl | N(C$_2$H$_5$)$_2$ | 189–190 |
| 18 | 6-CH$_3$ | 5-methyl-2-pyridyl | NH$_2$ | 270–271 |
| 19 | 6-CH$_3$ | 5-methyl-2-pyridyl | NHCH$_3$ | 222–223 |
| 20 | 6-CH$_3$ | 5-methyl-2-pyridyl | N(CH$_3$)$_2$ | 219–220 |
| 21 | 6-CH$_3$ | 5-chloro-2-pyridyl | NH$_2$ | 264–265 |
| 22 | 6-Cl | 5-bromo-2-furyl | OH | 255–256 |
| 23 | 6-CH$_3$ | 5-bromo-2-furyl | OH | 249–250 |
| 24 | 6-CH$_3$ | 5-methyl-2-furyl | OH | 244–245 |
| 25 | 6-CH$_3$ | 5-methyl-2-thienyl | OH | 230–231 |
| 26 | 6-CH$_3$ | 5-ethyl-2-thienyl | OH | 208–210 |
| 27 | 6-Cl | 5-chloro-2-thienyl | OH | 241–242 |
| 28 | 6-CH$_3$ | 5-chloro-2-thienyl | OH | 220–221 |
| 29 | 6-Cl | 2-pyridyl | OH | 212–213 |
| 30 | 6-CH$_3$ | 5-methyl-2-pyridyl | OH | 215–216 |

TABLE-continued $$\text{(I)}$$

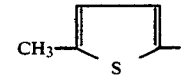

| Compound | Y | Z | R | Melting Point (°C.) |
|---|---|---|---|---|
| 31 | 6-CH₃ |  Cl-pyridine | OH | 228–230 |
| 32 | 6-Cl | pyridine | OC₂H₅ | 148–149 |
| 33 | 6-CH₃ | Cl-pyridine | OC₂H₅ | 184–185 |
| 34 | 6-Cl | Cl-pyridine | OC₃)₅ | 198–199 |
| 35 | 6-CH₃ | CH₃-pyridine | OC₂H₅ | 146–147 |
| 36 | 6-Cl | Cl-pyridine | OH | 230–235 |

The starting nitriles of general formula (II) are new compounds and as such form part of the invention.

The nitrile compounds prepared as Examples are shown in the following Table II.

TABLE II

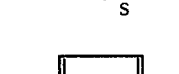

| Compound | Y | Z | Melting Point (°C.) |
|---|---|---|---|
| 1 | 6-Cl | Br-furan | 217–219 |
| 2 | 6-CH₃ | Br-furan | 215–217 |
| 3 | 6-CH₃ | CH₃-furan | 217–218 |

TABLE II-continued

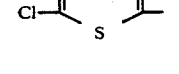

| Compound | Y | Z | Melting Point (°C.) |
|---|---|---|---|
| 4 | 6-CH₃ | CH₃-thiophene | 185–186 |
| 5 | 6-CH₃ | C₂H₅-thiophene | 195–196 |
| 6 | 6-Cl | Cl-thiophene | 202–204 |
| 7 | 6-CH₃ | Cl-thiophene | 167–169 |
| 8 | 6-Cl | pyridine | 224–225 |
| 9 | 6-CH₃ | CH₃-pyridine | 196–197 |
| 10 | 6-CH₃ | Cl-pyridine | 232–233 |
| 11 | 6-Cl | Cl-pyridine | 226–227 |

The compounds of the invention were subjected to pharmacological tests, which showed their valuable pharmacological properties in various fields.

The toxicity of the compounds was determined on mice by intraperitoneal administration. The LD50 ranges from 500 to 1000 mg/kg animal body weight.

The anxiolytic activity was determined by the "eating test" (R. J. Stephens (1973) Brit. J. Pharmac., 49, 146 P). In this test, the doses which increase the food consumption of the mice vary from 1 to 30 mg/kg, administered intraperitoneally.

The activity of the compounds in the field of the brain circulation was determined in the test for hypoxia caused by pressure reduction.

Mice of the CD1 strain are kept in an oxygen-depleted atmosphere produced by creating a partial vacuum (190 mm of mercury, corresponding to 5.25% of oxygen).

The survival time of the animals is noted. This time is increased by agents which are capable of assisting the oxygenation of tissues and in particular of the brain. The compounds studied are administered intraperitoneally in several doses, 10 minutes before the test. The percentage increases in the survival time, relative to the values obtained for control animals, are calculated. The mean active dose (MAD), that is to say the dose which increases the survival time by 100%, is determined graphically. The MAD ranges from 0.3 to 32 mg/kg, administered intraperitoneally.

The anticonvulsant activity was determined by the test for antagonism towards the mortality induced by bicuculline in mice (P. Worms, H. Depoortere and K. G. Lloyd (1979) Life Sci., 25, 607-614). The products to be studied are injected intraperitoneally, 30 minutes before the bicuculline (0.9 mg/kg, admininstered intravenously). As the criterion chosen for this test is lethality, the percentage mortalities are noted for each batch, 2 hours after administration of the bicuculline (control batch: 100% mortality).

The 50% active dose (AD50, that is to say the dose which protects 50% of animals from the lethal effects of the bicuculline) is determined graphically for each product. The AD50 of the compounds of the invention varies between 1 and 30 mg/kg, administered intraperitoneally.

The sedative or hypnotic activity was determined by observing the action of the compounds on the ECG of curarised rats (H. Depoortere, Rev. E.E.G. Neurophysiol., (1980) 10, 3, 207-214). The products to be studied were injected intraperitoneally or orally into the curarised rats, at increasing doses from 1 to 30 mg/kg. They induce sleep trances as from doses ranging from 1 to 10 mg/kg, administered intraperitoneally or orally.

The results of these various tests show that the compounds of the invention possess anxiolytic, antianoxic, sleep-inducing, hypnotic and anticonvulsant properties. The compounds of the invention are useful for the treatment of anxiety states, sleep disorders and other neurological and psychiatric complaints, for the treatment of vigilance disorders, in particular for combating the behavioural disorders attributable to cerebral vascular damage and to the cerebral sclerosis encountered in geriatrics, and also for the treatment of the absences due to cranial traumatisms and for the treatment of metabolic encephalopathies.

The present invention consequently includes within its scope pharmaceutical compositions containing, as active ingredient, an imidazo[1,2-a]pyridine derivative of general formula (I), or a pharmaceutically-acceptable acid addition salt thereof, in association with any suitable excipient.

The compounds of the invention can be presented in any form suitable for oral or parenteral administration, for example in the form of tablets, coated tablets, gelatine capsules, solutions to be taken orally or injected, and the like, with any suitable excipient.

The daily dosage can range from 0.5 to 2000 mg. of imidazo[1,2-a]pyridine derivative.

We claim:

1. An imidazo[1,2-a]pyridine derivative of the formula:

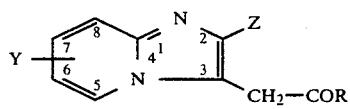

wherein Y represents a hydrogen or halogen atom or a $C_{1-4}$ alkyl radical, Z represents a furan-2-yl, thien-2-yl or pyridin-2-yl radical optionally carrying a halogen atom or a methyl or ethyl radical in the 5-position, and R represents the hydroxy radical, a $C_{1-4}$ alkoxy radical or a group $-NR_1R_2$ in which $R_1$ and $R_2$ independently of one another each represent a hydrogen atom; a straight- or branched-chain $C_{1-5}$ alkyl radical optionally carrying one or more halogen atoms or a hydroxy radical, a group $-N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical, or alternatively-$NR_1R_2$ together represent a heterocyclic ring containing from 3 to 6 carbon atoms, or a heterocyclic ring of the formula

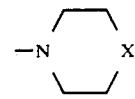

in which X is O, S, CHOR' or N-R'', R' being a hydrogen atom or the benzyl radical and R'' being a hydrogen atom, a $C_{1-4}$ alkyl radical or the phenyl radical optionally carrying a methoxy radical or a halogen atom, and pharmaceutically-acceptable acid addition salts thereof.

2. An imidazo[1,2-a]pyridine derivative according to claim 1 wherein R represents the hydroxy radical, a $C_{1-4}$ alkoxy radical or a group $-NR_1R_2$ in which $R_1$ and $R_2$ both represent hydrogen atoms, or $R_1$ represents a hydrogen atom and $R_2$ represents a $C_{1-5}$ alkyl radical, or $R_1$ and $R_2$ both represent $C_{1-5}$ alkyl radicals.

3. An imidazo[1,2-a]pyridine derivative according to claim 1 or 2 wherein the symbol R represents a group $-NR_1R_2$ in which $R_1$ and $R_2$ are both hydrogen atoms or $C_{1-5}$ alkyl radicals.

4. An imidazo[1,2-a]pyridine derivative according to claim 1 or 2 wherein R represents an amino, monomethylamino, dimethylamino, diethylamino or dipropylamino group.

5. An imidazo[1,2-a]pyridine derivative according to claim 2, 3 or 4 wherein Y in the general formula depicted in claim 1 represents a halogen atom or the methyl radical.

6. An imidazo[1,2-a]pyridine derivative according to any one of claims 1 to 5 wherein Z in the general formula depicted in claim 1 represents a thien-2-yl radical carrying a halogen atom or a methyl or ethyl radical in the 5-position.

7. An imidazo[1,2-a]pyridine derivative according to claim 1 which is 6-methyl-N,N-dimethyl-2-(5-methylthien-2-yl)-imidazo[1,2-a]pyridine-3acetamide and its pharmaceutically-acceptable acid addition salts.

8. An imidazo[1,2-a]pyridine derivative according to claim 1 which is 6-methyl-N,N-dimethyl-2-(5-ethylthien-2-yl)-imidazo[1,2-a]pyridine-3acetamide and its pharmaceutically-acceptable acid addition salts.

9. An imidazo[1,2-a]pyridine derivative according to claim 1 which is 6-chloro-N,N-dimethyl-2-(5-chlorothien-2-yl)-imidazo[1,2-a]pyridine-3-acetamide and its pharmaceutically-acceptable acid addition salts.

10. An imidazo-[1,2-a]pyridine derivative according to claim 1 which is 6-chloro-N,N-dipropyl-2-(5-chlorothien-2-yl)-imidazo[1,2-a]pyridine-3-acetamide and its pharmaceutically-acceptable acid addition salts.

11. A pharmaceutical composition for treating anxiety states which comprises, as active ingredient, an anxiolytic amount of imidazo[1,2-a]pyridine derivative as claimed in claim 1, or a pharmaceutically-acceptable acid addition salt thereof, in association with a pharmaceutically-acceptable vehicle.

12. A method for the treatment of anxiety states, sleep disorders, and behavioural disorders attributable to cerebral vascular damage and to the cerebral sclerosis encountered in geriatrics, which comprises administering to a patient with such an ailment an amount of an imidazo[1,2-a]-pyridine derivative of the formula depicted in claim 1, wherein Y, Z and R are defined in claim 1, or a pharmaceutically-acceptable acid addition salt thereof, sufficient to ameliorate the condition of the patient.

* * * * *